United States Patent [19]

Payne et al.

[11] Patent Number: 5,262,159

[45] Date of Patent: Nov. 16, 1993

[54] **USE OF *BACILLUS THURINGIENSIS* ISOLATES FOR CONTROLLING PESTS IN THE FAMILY APHIDIDAE**

[75] Inventors: Jewel M. Payne, San Diego, Calif.; Raymond J. C. Cannon, Sittingbourne, United Kingdom.

[73] Assignee: Mycogen Corporation, San Diego, Calif.

[21] Appl. No.: 935,310

[22] Filed: Aug. 24, 1992

[51] Int. Cl.$^5$ ............................................. C12N 1/20
[52] U.S. Cl. .............................. 424/93 L; 435/252.5; 435/832; 935/74
[58] Field of Search ................. 435/252.5, 832, 74; 424/93 L

[56] References Cited

U.S. PATENT DOCUMENTS

| | | | |
|---|---|---|---|
| 4,771,131 | 9/1988 | Hernstadt et al. | 435/172.3 |
| 4,849,217 | 7/1989 | Soares et al. | 424/93 |
| 4,948,734 | 8/1990 | Edwards et al. | 435/252.5 |
| 4,996,155 | 2/1991 | Sick et al. | 435/252.3 |
| 5,186,934 | 2/1993 | Narva et al. | 435/69.1 |

OTHER PUBLICATIONS de Barjec, H. (1990) "Characterization and Prospective View of *Bacillus thuringiensis israelensis*," In *Bacterial Control of Mosquitoes and Blackflies*, H. de Barjec, D. J. Sutherland (eds.), Rutgers University Press, pp. 10–15.

*Primary Examiner*—23021Robert A.
*Assistant Examiner*—D. B. Schmickel
*Attorney, Agent, or Firm*—Saliwanchik & Saliwanchik

[57] ABSTRACT

The subject invention concerns *Bacillus thuringiensis* isolates designated B.t. PS157C1, B.t. PS86A1, and B.t. PS75J1, which are active against aphid pests. Thus, these isolates, or variants thereof, can be used to control such pests. Further, genes encoding novel δ-endotoxins can be removed from these isolates and transferred to other host microbes, or plants. Expression of the δ-endotoxins in microbe hosts results in the control of aphid pests, whereas transformed plants become resistant to aphid pests.

2 Claims, 2 Drawing Sheets kDa

205

116
97.4

66

45

29

A  B  C

A. Bacillus thuringiensis PS75J1
B. Bacillus thuringiensis PS86A1
C. Bacillus thuringiensis PS157C1

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1425 base pairs
        ( B ) TYPE: nucleic acid
        ( C ) STRANDEDNESS: double
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: BACILLUS THURINGIENSIS
        ( C ) INDIVIDUAL ISOLATE: PS86A1

( v i i ) IMMEDIATE SOURCE:
        ( A ) LIBRARY: E. coli NM522

( i x ) FEATURE:
        ( A ) NAME/KEY: matpeptide
        ( B ) LOCATION: 1..1425

( x i ) SEQUENCE DESCRIPTION: SEQ ID NO:1:

```
ATGATTATTG  ATAGTAAAAC  GACTTTACCT  AGACATTCAC  TTATTCATAC  AATTAAATTA        60
```

-continued

| | | | | |
|---|---|---|---|---|
| AATTCTAATA | AGAAATATGG | TCCTGGTGAT | ATGACTAATG | GAAATCAATT  TATTATTTCA | 120 |
| AAACAAGAAT | GGGCTACGAT | TGGAGCATAT | ATTCAGACTG | GATTAGGTTT  ACCAGTAAAT | 180 |
| GAACAACAAT | TAAGAACACA | TGTTAATTTA | AGTCAGGATA | TATCAATACC  TAGTGATTTT | 240 |
| TCTCAATTAT | ATGATGTTTA | TTGTTCTGAT | AAAACTTCAG | CAGAATGGTG  GAATAAAAAT | 300 |
| TTATATCCTT | TAATTATTAA | ATCTGCTAAT | GATATTGCTT | CATATGGTTT  TAAAGTTGCT | 360 |
| GGTGATCCTT | CTATTAAGAA | AGATGGATAT | TTTAAAAAAT | TGCAAGATGA  ATTAGATAAT | 420 |
| ATTGTTGATA | ATAATTCCGA | TGATGATGCA | ATAGCTAAAG | CTATTAAAGA  TTTTAAAGCG | 480 |
| CGATGTGGTA | TTTTAATTAA | AGAAGCTAAA | CAATATGAAG | AAGCTGCAAA  AAATATTGTA | 540 |
| ACATCTTTAG | ATCAATTTTT | ACATGGTGAT | CAGAAAAAAT | TAGAAGGTGT  TATCAATATT | 600 |
| CAAAAACGTT | TAAAAGAAGT | TCAAACAGCT | CTTAATCAAG | CCCATGGGGA  AAGTAGTCCA | 660 |
| GCTCATAAAG | AGTTATTAGA | AAAAGTAAAA | AATTTAAAAA | CAACATTAGA  AAGGACTATT | 720 |
| AAAGCTGAAC | AAGATTTAGA | GAAAAAGTA  | GAATATAGTT | TTCTATTAGG  ACCATTGTTA | 780 |
| GGATTTGTTG | TTTATGAAAT | TCTTGAAAAT | ACTGCTGTTC | AGCATATAAA  AAATCAAATT | 840 |
| GATGAGATAA | AGAAACAATT | AGATTCTGCT | CAGCATGATT | TGGATAGAGA  TGTTAAAATT | 900 |
| ATAGGAATGT | TAAATAGTAT | TAATACAGAT | ATTGATAATT | TATATAGTCA  AGGACAAGAA | 960 |
| GCAATTAAAG | TTTTCCAAAA | GTTACAAGGT | ATTTGGGCTA | CTATTGGAGC  TCAAATAGAA | 1020 |
| AATCTTAGAA | CAACGTCGTT | ACAAGAAGTT | CAAGATTCTG | ATGATGCTGA  TGAGATACAA | 1080 |
| ATTGAACTTG | AGGACGCTTC | TGATGCTTGG | TTAGTTGTGG | CTCAAGAAGC  TCGTGATTTT | 1140 |
| ACACTAAATG | CTTATTCAAC | TAATAGTAGA | CAAAATTTAC | CGATTAATGT  TATATCAGAT | 1200 |
| TCATGTAATT | GTTCAACAAC | AAATATGACA | TCAAATCAAT | ACAGTAATCC  AACAACAAAT | 1260 |
| ATGACATCAA | ATCAATATAT | GATTTCACAT | GAATATACAA | GTTACCAAA   TAATTTTATG | 1320 |
| TTATCAAGAA | ATAGTAATTT | AGAATATAAA | TGTCCTGAAA | ATAATTTAT   GATATATTGG | 1380 |
| TATAATAATT | CGGATTGGTA | TAATAATTCG | GATTGGTATA | ATAAT | 1425 |

( 2 ) INFORMATION FOR SEQ ID NO:2:

( i ) SEQUENCE CHARACTERISTICS:
        ( A ) LENGTH: 475 amino acids
        ( B ) TYPE: amino acid
        ( C ) STRANDEDNESS: single
        ( D ) TOPOLOGY: linear     ( i i ) MOLECULE TYPE: protein     ( i i i ) HYPOTHETICAL: YES     ( i v ) ANTI-SENSE: NO     ( v i ) ORIGINAL SOURCE:
        ( A ) ORGANISM: BACILLUS THURINGIENSIS
        ( C

|   | 50 |   |   |   | 55 |   |   |   | 60 |   |   |   |   |
|---|----|---|---|---|----|---|---|---|----|---|---|---|---|

Arg Thr His Val Asn Leu Ser Gln Asp Ile Ser Ile Pro Ser Asp Phe
65                       70                  75                  80

Ser Gln Leu Tyr Asp Val Tyr Cys Ser Asp Lys Thr Ser Ala Glu Trp
                    85                  90                  95

Trp Asn Lys Asn Leu Tyr Pro Leu Ile Ile Lys Ser Ala Asn Asp Ile
                100                 105                 110

Ala Ser Tyr Gly Phe Lys Val Ala Gly Asp Pro Ser Ile Lys Lys Asp
            115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
    355                 360                 365

Ala Trp Leu Val Val Ala Gln Glu Ala Arg Asp Phe Thr Leu Asn Ala
370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
    435                 440                 445

Tyr Lys Cys Pro Glu Asn Asn Phe Met Ile Tyr Trp Tyr Asn Asn Ser
450                 455                 460

Asp Trp Tyr Asn Asn Ser Asp Trp Tyr Asn Asn
465                 470                 475

( 2 ) INFORMATION FOR SEQ ID NO:3:

(i) SEQUENCE CHARACTERISTICS:
 (A) LENGTH: 10 amino acids
 (B) TYPE: amino acid
 (C) STRANDEDNESS: single
 (D) TOPOLOGY: linear (ii) MOLECULE TYPE: protein (xi) SEQUENCE DESCRIPTION: SEQ ID NO:3:

```
Xaa  Asp  Phe  Xaa  Gln  Leu  Tyr  Xaa  Val  Tyr
 1              5                         10
```

(2) INFORMATION FOR SEQ ID NO:4:

(i) SEQUENCE CHARACTERISTICS:
 (A) LENGTH: 7 amino acids
 (B) TYPE: amino acid
 (C) STRANDEDNESS: single
 (D) TOPOLOGY: linear (ii) MOLECULE TYPE: protein (xi) SEQUENCE DESCRIPTION: SEQ ID NO:4:

```
Xaa  Glu  Leu  Leu  Xaa  Lys  Val
 1              5
```

(2) INFORMATION FOR SEQ ID NO:5:

(i) SEQUENCE CHARACTERISTICS:
 (A) LENGTH: 12 amino acids
 (B) TYPE: amino acid
 (C) STRANDEDNESS: single
 (D) TOPOLOGY: linear (ii) MOLECULE TYPE: protein (xi) SEQUENCE DESCRIPTION: SEQ ID NO:5:

```
Leu  Gly  Pro  Leu  Leu  Gly  Phe  Val  Val  Tyr  Glu  Ile
 1              5                         10
```

(2) INFORMATION FOR SEQ ID NO:6:

(i) SEQUENCE CHARACTERISTICS:
 (A) LENGTH: 9 amino acids
 (B) TYPE: amino acid
 (C) STRANDEDNESS: single
 (D) TOPOLOGY: linear (ii) MOLECULE TYPE: protein (xi) SEQUENCE DESCRIPTION: SEQ ID NO:6:

```
Asp  Arg  Asp  Val  Lys  Ile  Xaa  Gly  Met
 1              5
```

(2) INFORMATION FOR SEQ ID NO:7:

(i) SEQUENCE CHARACTERISTICS:
 (A) LENGTH: 8 amino acids
 (B) TYPE: amino acid
 (C) STRANDEDNESS: single
 (D) TOPOLOGY: linear (ii) MOLECULE TYPE: protein (xi) SEQUENCE DESCRIPTION: SEQ ID NO:7:

```
Xaa  Xaa  Lys  Xaa  Ala  Asn  Asp  Ile
 1              5
```

(2) INFORMATION FOR SEQ ID NO:8:

(i) SEQUENCE CHARACTERISTICS:

(A) LENGTH: 20 amino acids
(B) TYPE: amino acid
(D) TOPOLOGY: linear (ii) MOLECULE TYPE: peptide (vi) ORIGINAL SOURCE:
(A) ORGANISM: Bacillus thuringiensis
(B) STRAIN: PS86A1

(xi) SEQUENCE DESCRIPTION: SEQ ID NO:8:

```
Met Ile Ile Asp Ser Lys Thr Thr Leu Pro Arg His Ser Leu Ile His
 1               5                  10                  15
Thr Ile Lys Leu
            20
```

(2) INFORMATION FOR SEQ ID NO:9:

(i ) SEQUENCE CHARACTERISTICS:
( A ) LENGTH: 53 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus thuringiensis
( B ) STRAIN: PS86A1

( x i ) SEQUENCE DESCRIPTION: SEQ ID NO:9:

```
ATGATTGATT CTAAAACAAC ATTACCAAGA CATTCWTTAA TWCATACWAT WAA    53
```

( 2 ) INFORMATION FOR SEQ ID NO:10:

( i ) SEQUENCE CHARACTERISTICS:
( A ) LENGTH: 28 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:10:

```
TGATTTTWMT CAATTATATR AKGTTTAT    28
```

( 2 ) INFORMATION FOR SEQ ID NO:11:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:11:

```
AAGAGTTAYT ARARAAAGTA    20
```

( 2 ) INFORMATION FOR SEQ ID NO:12:

( i ) SEQUENCE CHARACTERISTICS:
( A ) LENGTH: 35 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:12:

```
TTAGGACCAT TRYTWGGATT TGTTGTWTAT GAAAT    35
```

(2) INFORMATION FOR SEQ ID NO:13:

(i) SEQUENCE CHARACTERISTICS:
  (A) LENGTH: 27 bases
  (B) TYPE: nucleic acid
  (C) STRANDEDNESS: single
  (D) TOPOLOGY: linear  (ii) MOLECULE TYPE: DNA (synthetic)

(xi) SEQUENCE DESCRIPTION: SEQ ID NO:13:

GAYAGAGATG TWAAAATYWT AGGAATG     27

(2) INFORMATION FOR SEQ ID NO:14:

(i) SEQUENCE CHARACTERISTICS:
  (A) LENGTH: 23 bases
  (B) TYPE: nucleic acid
  (C) STRANDEDNESS: single
  (D) TOPOLOGY: linear  (ii) MOLECULE TYPE: DNA (synthetic)

(xi) SEQUENCE DESCRIPTION: SEQ ID NO:14:

TTMTTAAAWC WGCTAATGAT ATT     23

USE OF *BACILLUS THURINGIENSIS* ISOLATES FOR CONTROLLING PESTS IN THE FAMILY APHIDIDAE

BACKGROUND OF THE INVENTION

The spore-forming microorganism *Bacillus thuringiensis* (B.t.) produces the best-known insect toxin. The toxin is a protein, designated as δ-endotoxin. It is synthesized by the B.t. sporulating cell. The toxin, upon being ingested in its crystalline form by susceptible insect larvae, is transformed into biologically active moieties by the insect gut juice proteases. The primary target is insect cells of the gut epithelium, which are rapidly destroyed. Experience has shown that the activity of the B.t. toxin is so high that only nanogram amounts are required to kill susceptible insects.

The reported activity spectrum of B.t. covers insect species within the order Lepidoptera, which is a major insect problem in agriculture and forestry. The activity spectrum also includes the insect order Diptera, wherein reside mosquitoes and blackflies. See de Barjac, H. ([1990] In H. de Barjac, D. J. Sutherland (eds.) *Bacterial Control of Mosquitoes and Blackflies*, Rutgers University Press, Chapter 2). U.S. Pat. Nos. 4,771,131 and 4,996,155 disclose toxin genes which are active against beetles of the order Coleoptera. Activity has also been reported outside the class Insecta. B.t. strains having activity against nematodes were disclosed in U.S. Pat. No. 4,948,734.

Aphids (Order Hemiptera, Family Aphididae) are sucking insects that are damaging to many economically important plants. Plant damage occurs when aphids infest plants in high numbers. Because aphids can reproduce by parthenogenesis, aphid populations have the potential to increase rapidly. High numbers of aphids can contribute to fungal infestations. In addition to the damage caused by aphid feeding, aphids can vector many viral diseases of plants.

Economically important aphids include the green peach aphid (*Myzus persicae*), pea aphid (*Acyrthosiphon pisum*), cabbage aphid (*Brevicoryne brassicae*), cotton aphid (*Aphis gossypii*), and black bean aphid (*Aphis fabae*).

BRIEF SUMMARY OF THE INVENTION

The subject invention concerns *Bacillus thuringiensis* isolates which have aphidicidal properties. More specifically, the subject invention concerns the use of *Bacillus thuringiensis* isolates designated B.t. PS157C1 (also known as B.t. MT104), B.t. PS86A1, and B.t. PS75J1 to control aphids in the environment.

The aphidicidal use of the B.t. isolates of the invention is shown herein, by way of example, by their activity against the pea aphid *Acyrthosiphon pisum*. Thus, these isolates can be used to control this aphid, and other aphids in the family Aphididae. Further, the δ-endotoxins from these B.t. isolates can be isolated by standard procedures, e.g. ion exchange, and formulated by standard procedures to control these insect pests. Still further, the gene(s) from the B.t. isolates of the invention which encode the aphidicidal toxin can be cloned from the isolates and then used to transform other hosts, e.g., prokaryotic, eukaryotic or plants, which transformed host can be used to control aphids, or, in the case of transgenic plants, be resistant to aphids.

Specifically exemplified herein is the cloning of gene 86A1 obtainable from B.t. PS86A1. Using the teachings of the subject invention, a person skilled in the art could identify other B.t. aphidicidal toxins, as well as the genes which code for such toxins.

BRIEF DESCRIPTION OF THE SEQUENCES

SEQ ID NO. 1 is the DNA sequence of a gene of B.t. PS86A1.

SEQ ID NO. 2 is the amino acid sequence of the toxin encoded by a gene of B.t. PS86A1.

SEQ ID NO. 3 is a peptide sequence according to the subject invention.

SEQ ID NO. 4 is a peptide sequence according to the subject invention.

SEQ ID NO. 5 is a peptide sequence according to the subject invention.

SEQ ID NO. 6 is a peptide sequence according to the subject invention.

SEQ ID NO. 7 is a peptide sequence according to the subject invention.

SEQ ID NO. 8 is an N-terminal amino acid sequence of 86A1.

SEQ ID NO. 9 is an oligonucleotide probe designed from SEQ ID NO. 3, designated 86A1-A.

SEQ ID NO. 10 is a nucleotide sequence according to the subject invention.

SEQ ID NO. 11 is a nucleotide sequence according to the subject invention.

SEQ ID NO. 12 is a nucleotide sequence according to the subject invention.

SEQ ID NO. 13 is a nucleotide sequence according to the subject invention.

SEQ ID NO. 14 is a nucleotide sequence according to the subject invention.

DETAILED DISCLOSURE OF THE INVENTION

The subject invention concerns isolates of *Bacillus thuringiensis* having aphidicidal activity. These isolates comprise genes which code for δ-endotoxins, which toxins are responsible for the observed aphidicidal activity. Thus, the subject invention concerns aphidicidal B.t. isolates, aphidicidal B.t. toxins, and genes which code for these toxins. Further embodiments of the subject invention concern recombinant hosts transformed with genes coding for the aphidicidal B.t. toxins. In a preferred embodiment, the transformed host is a plant which, by virtue of its transformation with the B.t. gene, is resistant to aphids. The subject invention further concerns methods for controlling aphids, said methods comprising the use of the isolates, toxins, genes, and recombinant hosts of the subject invention.

Specifically exemplified herein are the isolates designated B.t. PS157C1, B.t. PS86A1, and B.t. PS75J1. Also specifically exemplified is the toxin designated 86A1 and the gene which codes for this toxin. The discovery described in the subject application also enables a person skilled in the art to identify other toxins (and genes coding for these toxins) having aphidicidal activity. The toxins of the subject invention are characterized as being aphidicidal and having one or more of the following characteristics:

1. A high degree of amino acid homology with toxin 86A1.
2. A nucleotide sequence encoding the toxin wherein the nucleotide sequence hybridizes with probes or genes disclosed herein.
3. A nucleotide sequence encoding the toxin wherein the nucleotide sequence can be amplified by PCR using primers disclosed herein.
4. An amino acid sequence which conforms to the Generic Formula presented herein.
5. Immunoreactivity to an antibody raised to toxin 86A1.

The B.t. isolates of the invention have characteristics which distinguish then from previously-known B.t. isolates. Table 1 shows a comparison of the B.t. isolates of the subject invention with two well-known B.t. strains, B.t. HD-1 and B.t.s.d.

TABLE 1

Comparison of *B.t.* PS75J1, *B.t.* PS86A1, *B.t.* PS157C1, *B.t.s.d.*, and *B.t.* HD-1

|  | *B.t.* PS75J1 | *B.t.* PS86A1 | *B.t.* PS157C1 | *B.t.* HD-1 | *B.t.s.d.* |
|---|---|---|---|---|---|
| Inclusions: | Amorphic | Multiple | Flat square and bipyramid | Bipyramid | Flat square |
| Approximate molecular wt. of proteins by SDS-PAGE | 81,000 79,000 75,000 63,000 | 58,000 45,000 | 130,000 72,000 64,000 | 130,000 68,000 | 72,000 64,000 |
| Serotype | wuhenenis | wuhenensis | morrisoni | kurstaki | morrisoni |
| Host range | Aphid, Mite, Coleoptera (AW, CRW, RFB) | Aphid, Mite, Coleoptera (AW, CRW, RFB) | Aphid, Lepidoptera, Coleoptera (CPB) | Lepidoptera | Coleoptera (CPB) |

CPB = Colorado Potato Beetle;
AW = Alfalfa Weevil;
CRW = Corn Rootworm;
RFB = Rape Flea Beetle Additionally, the isolates have the following common characteristics:
Colony morphology—large colony, dull surface, typical B.t.
Vegetative cell morphology—typical B.t.

The B.t. isolates of the invention, and variants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains. The novel B.t. isolates, and variants thereof, can be used to control target pests.

The cultures of the subject invention were deposited in the Agricultural Research Service Patent Culture Collection (NRRL), Northern Regional Research Center, 1815 North University Street, Peoria, Ill., 61604 USA.

| Culture | Accession No. | Deposit Date |
|---|---|---|
| *B.t.* PS75J1 | NRRL B-18781 | March 7, 1991 |
| *B.t.* PS86A1 | NRRL B-18400 | August 16, 1988 |
| *B.t.* PS157C1 (a.k.a. MT104) | NRRL B-18240 | July 17, 1987 |
| *E. coli* NM522[pMYC2320] | NRRL B-18769 | February 14, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits are stored and made available to the public in accord with the provisions of the Budapest Treaty for the Deposit of Microorganisms, i.e., they are stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

The invention also includes variants of the subject isolates which variants have genes encoding all or part of a toxin of the invention or other toxin having aphidicidal activity. Such microbial variants may be isolated or they can be made by techniques well known to persons skilled in the art. For example, UV irradiation can be used to prepare variants of host organisms. Likewise, such variants may include asporogenous host cells which also can be prepared by procedures well known in the art. For example, an asporogenous mutant can be obtained through ethylmethane sulfonate (EMS) mutagenesis of a novel isolate. A small percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

The variants can also be made using ultraviolet light and nitrosoguanidine by procedures well known in the art.

Aphidicidal toxins of the subject invention are specifically exemplified herein by the toxin designated 86A1. The subject invention further comprises equivalent toxins (and nucleotide sequences coding for equivalent toxins) having the same or similar biological activity of 86A1. These equivalent toxins may have amino acid homology with the toxin disclosed and claimed herein. This amino acid homology will typically be greater than 50%, preferably be greater than 75%, and most preferably be greater than 90%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cyc, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin. It has been shown that proteins of identified structure and function may be constructed by changing the amino acid sequence if such changes do not alter the protein secondary structure (Kaiser, E. T. and Kezdy, F. J. [1984] *Science* 223:249–255). Thus, the subject invention includes mutants of the amino acid sequence depicted herein which do not alter the protein secondary structure, or if the structure is altered, the biological activity is substantially retained.

The genes and toxins according to the subject invention include not only the full length sequences disclosed herein but also fragments of these sequences, or fusion proteins, which retain the characteristic aphidicidal activity of the toxins specifically exemplified herein.

One aspect of the subject invention concerns the discovery of a generic chemical formula hereinafter referred to as the Generic Formula, which can be used to identify toxins having activity against aphids. The Generic Formula describes toxin proteins having molecular weights from about 45 kDa to about 65 kDa. Their primary amino acid structure substantially follows the motif illustrated below:

```
  1  ML̲BXXXXOBP    KHxxxXXXXO    XXXXZXKKxx    xXZPXXBXXX    XXBLLZKXEW
     OX̄BXOYBXOZ    XZL̲PBUJ XXB   KXHBXL̲X̄X̄JL̲   XL̲PXJ BXUL̲Y   J BYX̄X̄J K̲XX̄X 101  XWWUXXL̲XPL̲    BBKXOUJ L̲XX   YZBKXOZJ XX   KKxx ZXXJ XB  UJ J BJ UL̲XJ U
     XXJ J OXX̄X̄K̲O   XK̲J BXOK̲C̄XL̲  LL̲K̲E̲OJ UYJ X  OŌJ XBXXXL̲X   XBL̲XZXŪxxx 201  xXJ BXZBXXB    UXXL̲XXBXXX    LXXXXZJ XZP   XXJ EL̲L̲J KBJ  XL̲KXXL̲EXXL̲
     K̲OE̲UJ L̲EKKB   BXZB̄XL̲ZPL̲L̲    Z̄BBBYEL̲L̲EX   OOBX̄X̲L̲XX̄X̄B   J X̄L̲XXX̄L̲J XŌ

301  UXJ L̲J KJ BKL  LZBBUZL̲XOJ    L̲J XBXXUZXX   OL̲XBBXKL̲XZ   LWXXL̲XXUL̲X
     UL̲K̲X̄OZ̄XXE̲B    X̄J XXJ XJ̄ XL̲X  L̲EL̲XJ OXXXW   XX̄BOXE̲ŌXXB   X̄L̲UZY̲XXxxx 401  (x)n^a
```

^a Where n = 0–100

Numbering is for convenience and approximate location only.

Symbols used:

| | | | |
|---|---|---|---|
| A = ala | G = gly | M = met | S = ser |
| C = cys | H = his | N = asn | T = thr |
| D = asp | I = ile | P = pro | V = val |
| E = glu | K = lys | Q = gln | W = trp |
| F = phe | L = leu | R = arg | Y = tyr |

K̲ = K or R
E̲ = E or D
L̲ = L or I
B̄ = M, L, I, V, or F
J = K, R, E, or D
O = A or T
U = N or Q
Z = G or S
X = any naturally occurring amino acid, except C.
* = any naturally occurring amino acid.
x = any naturally occurring amino acid, except C (or complete omission of any amino acids).

Where a stretch of wild-card amino acids are encountered (X(n) or x(n) where n>2), repetition of a given amino acid should be avoided. Similarly, P, C, E, D, K, or R utilization should be minimized.

This formula is exemplified in the current application by the specific toxin 86A1.

It should be apparent to a person skilled in this art that genes coding for aphidicidal toxins can be identified and obtained through several means. The specific genes may be obtained from a culture depository as described herein. Alternatively, these genes, or portions thereof, may be constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be located from B.t. isolates and/or DNA libraries using the teachings provided herein. There are a number of methods for obtaining the aphidicidal toxins of the instant invention which occur in nature. For example, antibodies to the aphidical toxins disclosed and claimed herein can be used to identify and isolate other toxins from a mixture of proteins. These antibodies can then be used to specifically identify equivalent toxins with the characteristic aphidicidal activity by immunoprecipitation, enzyme linked immunoassay (ELISA), or Western blotting. Antibodies to the toxins disclosed herein, or to equivalent toxins, or fragments of these toxins, can readily be prepared using standard procedures in this art.

A further method for identifying the toxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying aphidicidal endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:
(1) synthesizing chemically or otherwise an artificial sequence which is a mutation, insertion or deletion of the known sequence;
(2) using a probe of the present invention to obtain via hybridization a new sequence or a mutation, insertion or deletion of the probe sequence; and
(3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

Specific nucleotide probes useful, according to the subject invention, in the rapid identification of aphidicidal genes are nucleotide sequences which code for the following amino acid sequences: "(D,S)DF(N,S)QLY(K,D)VY" (SEQ ID NO. 3); "(E,K)ELL(E,K)KV" (SEQ ID NO. 4); "LPGLLGFVVYEI" (SEQ ID NO. 5); "DRDVKI(L,I)GM" (SEQ ID NO. 6); and "(V,I)(L,I)K(T,S)ANDI" (SEQ ID NO. 7). Because of the redundancy of the genetic code, i.e., more than one coding nucleotide triplet (codon) can be used for most of the amino acids used to make proteins, different nucleotide sequences can code for a particular amino acid. Thus, the amino acid sequences of the B.t. toxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art.

The three-letter amino acid code shown in the Sequence Listing herein has no provision for reflection of the above single-letter amino acid sequences where there is a choice between two amino acids at a given position. Therefore, within the Sequence Listing, "Xaa" is used to denote points of variation within a sequence, but the above single letter code should be referred to for the specific amino acids at a given location in the sequence.

The pesticidal formulations of the subject invention can be applied to the environment of the target pest(s), e.g., plants, soil or water, by spraying, dusting, sprinkling, or the like. The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Upon applying an aphidicidal-effective amount of a microbe, or toxin, as disclosed herein, in a suitable aphidicidal formulation to the environment of the target pest, there is obtained effective control of these pests.

An aphidicidal-effective amount can vary from about 1 to about 12 l/ha, depending upon the nature and quantity of the pests to be controlled, the time of year, temperature, humidity, and other known factors which may affect a bioinsecticide. It is well within the skill of those trained in this art to determine the quantity of bioinsecticide to apply in order to obtain effective control of target pests.

The δ-endotoxin protein can be combined with other insecticidal proteins (including those obtained from sources other than *Bacillus thuringiensis*) to increase the spectrum of activity to give complete control of target pests.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The toxin genes harbored by the novel isolates of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of aphids where they will proliferate. The result is a control of the aphids.

The microbe hosting the toxin gene can be treated under conditions that prolong the activity of the toxin produced in the cell. Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like. The treated cell then can be applied to the environment of the target pest. The resulting product retains the toxicity of the B.t. toxin.

A wide variety of ways are available for introducing a B.t. gene expressing a toxin into the microorganism host under conditions which allow for stable maintenance and expression of the gene. These methods are well known to those skilled in the art.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing of the B.t. Isolates

A subculture of the B.t. isolates, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |

| Salts Solution (100 ml) | |
| --- | --- |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | 3.66 g |
| CaCl$_2$.2H$_2$O | |

The salts solution and CaCl$_2$ solution are filter-sterilized and added to the autoclaved and cooked broth at the time of inoculation. Flasks are incubated at 30° C. on a rotary shaker at 200 rpm for 64 hr. The parasporal inclusion bodies, spores, and cellular debris were collected by centrifugation (7.14 k*g* 20 min.).

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

N-Terminal Sequencing

The parasporal inclusion bodies were partially purified by sodium bromide (28–38% isopycnic gradient centrifugation (M. A. Pfannenstiel et al. [1984] *FEMS Microbiol. Lett.* 21:39). The partially purified protein was bound to the Immobilon-P, PVDF membrane (Millipore, Bedford, Mass.) by western blotting techniques (H. Towbin et al. [1979] *Proc. Natl. Acad. Sci. USA* 76:4350). The N-terminal amino acid sequence was determined by the standard Edman reaction with an automated gasphase sequenator (M. W. Hunkapiller et al. [1983] *Meth. Enzymol.* 91:399). The sequence obtained was as follows:

NH$_2$—MIIDSKTTLPRHSLIHTIKL—CO$_2$H    (SEQ ID NO. 8)

From this sequence, the following oligonucleotide probe was designed:

5' ATG ATT GAT TCT AAA ACA ACA TTA CCA AGA CAT TCT/A    (SEQ ID NO. 9)
TTA ATT/A CAT ACT/A ATT/A AA 3'

This probe was designated as 86A1-A.

EXAMPLE 3

*Molecular Cloning of Gene Encoding a Novel Toxin from Bacillus thuringiensis Strain PS86A1*

Total cellular DNA was prepared from PS86A1 cells grown to an optical density, at 600 nm, of 1.0. Cells were pelleted by centrifugation and resuspended in protoplast buffer (20 mg/ml lysozyme in 0.3M sucrose, 25 mM Tris-Cl, pH 8.0, 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE), pH 8.0, and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Restriction fragment length polymorphism (RFLP) analyses were performed by standard hybridization of southern blots of PS86A1 DNA with the $^{32}P$-labeled oligonucleotide probe designated as 86A1-A.

The probe was mixed at four positions, as shown. Hybridizing bands included an approximately 3.6 kbp HindIII fragment and an approximately 9.3 kbp EcoRV fragment.

A gene library was constructed from PS86A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega, Madison, Wis.). Recombinant phage were packaged and plated on *E. coli* KW251 cells (Promega). Plaques were screened by hybridization with the radiolabeled 86A1-A oligonucleotide probe. Hybridizing phage were plaque-purified and used to infect liquid cultures of *E. coli* KW251 cells for isolation of phage DNA by standard procedures (Maniatis et al. [1982]*Molecular Cloning: A Laboratory Manual*, Cold Spring Harbor Laboratory, Cold Spring Harbor, N.Y.). For subcloning, preparative amounts of DNA were digested with EcoRI and SalI, and electrophoresed on an agarose gel. The approximately 2.9 kbp band containing the toxin gene was excised from the gel, electroeluted from the gel slice, and purified by ion exchange chromatography as above. The purified DNA insert was ligated into EcoRI+SalI-digested pHTBlueII (an *E. coli*/B.t. shuttle vector comprised of pBlueScript S/K (Stratagene, San Diego, Calif.) and the replication origin from a resident B.t. plasmid (D. Lereclus et al. [1989] *FEMS Microbiol. Lett.* 60:211–218). The ligation mix was used to transform frozen, competent *E. coli* NM522 cells (ATCC 47000). Transformants were plated on LB agar (Maniatis et al., supra) containing ampicillin, isopropyl-(β)-D-thiogalactoside (IPTG), and 5-bromo-4-chloro-3-indolyl-(β)-D-galactoside (XGAL). Plasmids were purified from putative recombinants by alkaline lysis (Maniatis et al., supra) and analyzed by electrophoresis of EcoRI and SalI digests on agarose gels. The desired plasmid construct, pMYC2320, contains the toxin gene of the invention. See FIG. 2. The DNA sequence of this gene is shown in SEQ ID NO. 1. The toxin expressed by this gene is shown in SEQ ID NO. 2.

Plasmid pMYC2320 was introduced into an acrystalliferous ($Cry^-$) B.t. host (B.t. HD-1 cryB, A. I. Aronson, Purdue University, West Lafayette, Ind.) by electroporation. Expression of an approximately 58 kDa protein is verified by SDS-PAGE analysis.

The restriction enzymes disclosed herein can be purchased from Boehringer Mannheim, Indianapolis, Ind., or New England Biolabs, Beverly, Mass. The enzymes are used according to the instructions provided by the supplier.

Figure 1:
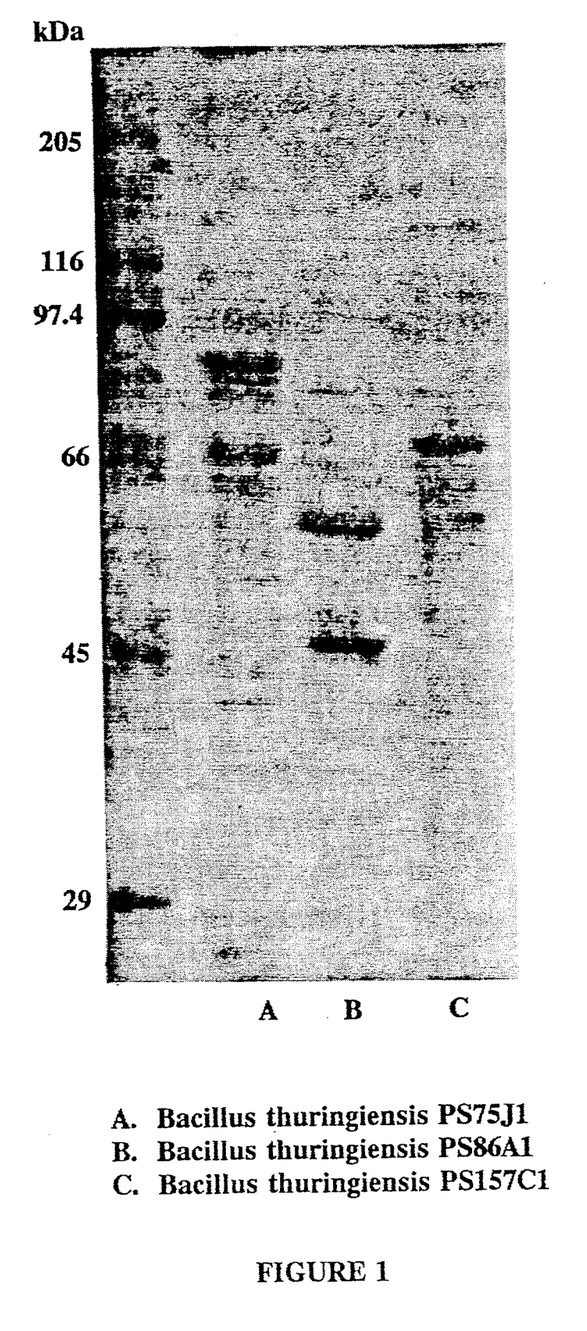
FIG. 1 is a photograph of a 12% SDS polyacrylamide gel showing alkali-soluble proteins of the isolates of the invention.
Figure 2:
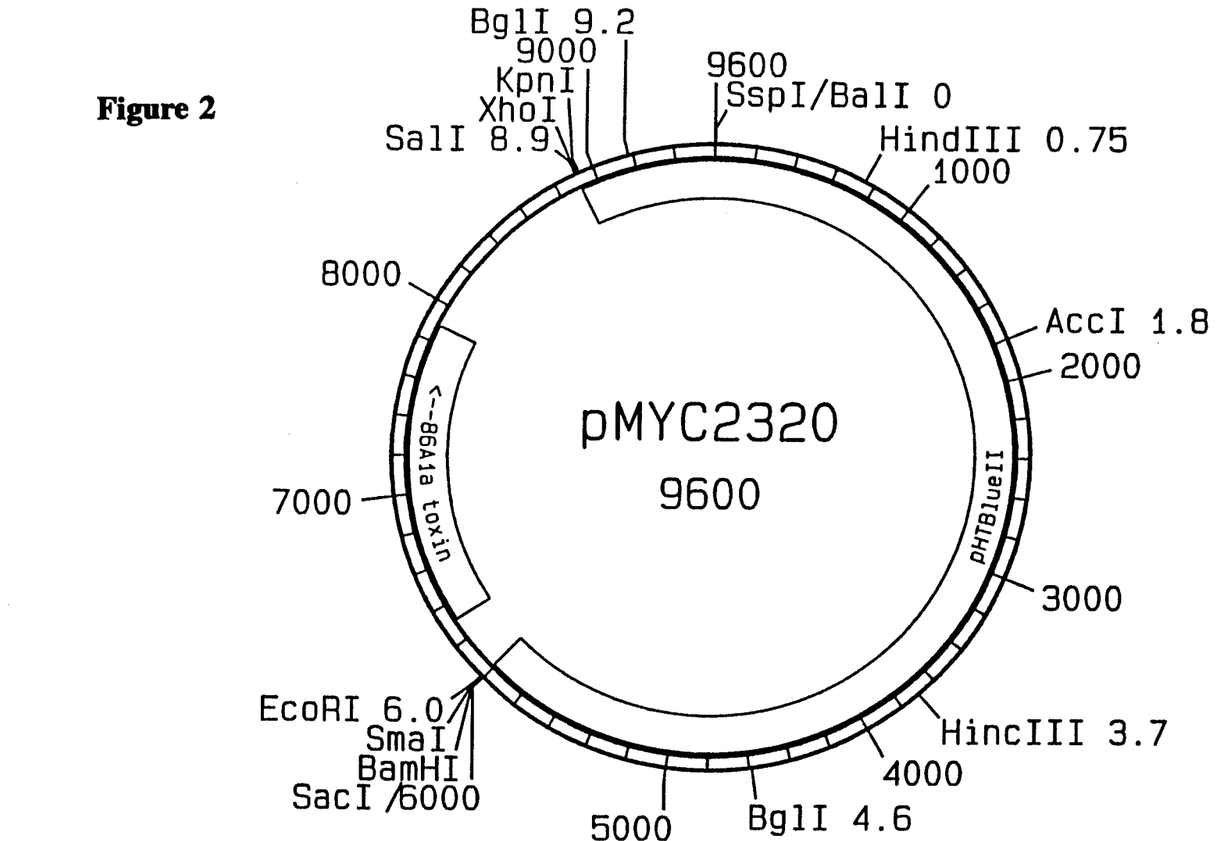
FIG. 2 is a restriction map of plasmid pMYC2320.

Plasmid pMYC2320 containing the B.t. toxin gene, can be removed from the transformed host microbe by use of standard well-known procedures. For example, *E. coli* NM522(pMYC2320) can be subjected to cleared lysate isopycnic density gradient procedures, and the like, to recover pMYC2320.

EXAMPLE 4

Further Cloning of Novel Aphid-Active Genes Using Generic Oligonucleotide Primers A gene coding for an aphidicidal toxin from a new aphidicidal B.t. isolate can be obtained from DNA of the strain by performing the standard polymerase chain reaction procedure using specific oligonucleotide primers as follows:

1. Forward primer "TGATTTT(T or A)(C or A)T-CAATTATAT(A or G)A(G or T)GTTTAT" (SEQ ID NO. 10) can be used with primers complementary to probe "AAGAGTTA(C or T)TA(A or G)A(G or A)AAAGTA" (SEQ ID NO. 11), probe "TTAGGAC-CATT(A or G)(C or T)T(T or A)GGATTTGTTG-T(A or T)TATGAAAT" (SEQ ID NO. 12), and probe "GA(C or T)AGAGATGT(A or T)AAAAT(C or T)(T or A)TAGGAATG" (SEQ ID NO. 13) to produce amplified fragments of approximately 440, 540, and 650 bp, respectively.

2. Forward primer "TT(A or C)TTAAA(A or T)C(A or T)GCTAATGATATT" (SEQ ID NO. 14) can be used with primers complementary to SEQ ID NO. 11, SEQ ID NO. 12, and SEQ ID NO. 13 to produce amplified fragments of approximately 360, 460, and 570 bp, respectively.

3. Forward primer SEQ ID NO. 11 can be used with primers complementary to SEQ ID NO. 12 and SEQ ID NO. 13 to produce amplified fragments of approximately 100 and 215 bp, respectively.

Amplified DNA fragments of the indicated sizes can be radiolabeled and used as probes to clone an entire gene as in Example 3.

It should be noted that each of the above-listed primers (SEQ ID NOS. 10–14) may also be used as probes for genes coding for aphidicidal toxins as described above.

EXAMPLE 5

Activity of B.t. Isolates Against the Pea Aphid (*Acyrthosiphon pisum*)

*B. thuringiensis* isolates of the invention were tested as spray-dried powders of fermentation broths which were concentrated by centrifugation. Pellets, which consist of water and biomass (spores, crystalline delta-endotoxins, cellular debris and growth media) were mixed with a standard carrier, preservative and surfactant. Powders, which consisted of 25% biomass, were made using a Yamato spray drier (sold by Yamata Scientific Co., Ltd. Tokyo, Japan).

All broths were tested for the presence of beta-exotoxin by a larval house fly bioassay (Campbell, D. P., Dieball, D. E. and Brackett, J. M., 1987, Rapid HPLC assay for the β-exotoxin of *Bacillus thuringiensis*. J. Agric. Food Chem. 35:156–158). Only isolates which tested free of β-exotoxin were used in the assays against aphids.

Suspensions of spray-dried powders were prepared for testing by mixing 25 mg of powder in 5 ml of a 10% sucrose solution. This mixture was then sonicated for 8 min to produce a suspension.

Two ml of suspension was placed in a reservoir consisting of a metal ring with a Parafilm ®M film bottom. A petri dish containing approximately 30 female pea aphids (*Acyrthosiphon pisum*) was placed on the underside of the film. Aphids were allowed to feed on the sucrose solution for 24 hrs and then transferred to pea seedlings. Mortality was determined after 4 days (Table 3). Each assay was done in triplicate. Table 3 shows toxicity of *Bacillus thuringiensis* isolates to pea aphids, *Acyrthosiphon pisum*, at 5000 ppm.

TABLE 3

| Isolate | Percent Mortality |
| --- | --- |
| B.t. PS157C1 | 100 |
| B.t. PS86A1 | 90 |
| B.t. PS75J1 | 100 |
| Control | 0 |

EXAMPLE 6

Insertion of Toxin Genes Into Plants

One aspect of the subject invention is the transformation of plants with genes coding for a aphidicidal toxin. The transformed plants are resistant to attack by nematodes.

Genes coding for aphidicidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence coding for the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B.V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 7

Cloning of Novel *B. thuringiensis* Genes Into Insect Viruses

A number of viruses are known to infect insects. These viruses include, for example, baculoviruses and entomopoxviruses. In one embodiment of the subject invention, ant-active genes, as described herein, can be placed with the genome of the insect virus, thus enhancing the pathogenicity of the virus. Methods for constructing insect viruses which comprise B.t. toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

---

We claim:

1. A method for controlling pests from the family Aphididae which comprises exposing said pests to an aphid-controlling effective amount of the *Bacillus thuringiensis* isolate designated B.t. PS86A1, or mutants or toxins of said isolate wherein said mutants or toxins retain the aphidicidal characteristics of B.t. PS86A1.

2. The method, according to claim 1, which comprises exposing said pests to B.t. PS86A1.

* * * * *

UNITED STATES PATENT AND TRADEMARK OFFICE
CERTIFICATE OF CORRECTION

PATENT NO. : 5,262,159
DATED : November 16, 1993
INVENTOR(S) : Jewel Payne and Raymond J.C. Cannon It is certified that error appears in the above-indentified patent and that said Letters Patent is hereby corrected as shown below:

Column 5-6, line 201 of sequence listing: Delete "LE" and insert --LE--.

Column 6, line 4 (Table 2): Delete "Cyc" and insert --Cys--.

Column 11 line 7: Move "3.66 g" to the next line after --CaCl$_2$ 2H$_2$0--.

Column 15, Sequence Listing, Section (2)(vii)(A): After "E. coli (NM522)" insert --[pMYC2320]--.

Column 15, Sequence Listing, Section (2)(ix)(A): Delete "matpeptide" and insert --mat peptide--.

Signed and Sealed this

Thirty-first Day of May, 1994

Attest:

BRUCE LEHMAN

*Attesting Officer*   *Commissioner of Patents and Trademarks*